United States Patent [19]

Fatool et al.

[11] Patent Number: 4,870,956
[45] Date of Patent: Oct. 3, 1989

[54] KNEE BRACE

[75] Inventors: Wade Fatool, Sunbury; Robert J. Ferraro, Winfield, both of Pa.

[73] Assignee: Competitive Athletics Technology, Inc., Winfield, Pa.

[21] Appl. No.: 222,528

[22] Filed: Jul. 21, 1988

[51] Int. Cl.$^4$ ................................................ A61F 3/00
[52] U.S. Cl. ................................... 128/80 C; 128/165
[58] Field of Search .................. 128/80 C, 80 F, 165; 2/24

[56] References Cited

U.S. PATENT DOCUMENTS

| | | | |
|---|---|---|---|
| 2,652,565 | 9/1953 | MacLellan | 2/24 |
| 3,074,400 | 1/1963 | Schulman | 2/24 |
| 3,473,527 | 10/1969 | Spiro | 128/80 C |
| 3,513,842 | 5/1970 | Keenan | 2/24 |
| 3,677,265 | 7/1972 | Brabazon | 2/24 |
| 3,965,486 | 6/1976 | Lightbody | 128/165 |
| 4,115,902 | 9/1978 | Taylor | 16/179 |
| 4,201,203 | 5/1980 | Applegate | 128/80 |
| 4,250,578 | 2/1981 | Barlow | 2/24 |
| 4,466,428 | 8/1934 | McCoy | 128/80 C |
| 4,607,628 | 8/1986 | Dashefsky | 128/80 C |
| 4,685,153 | 8/1987 | Sims | 2/24 |
| 4,700,698 | 10/1987 | Kleylein | 128/80 C |
| 4,756,026 | 7/1988 | Pierce | 2/24 |

FOREIGN PATENT DOCUMENTS

| | | | |
|---|---|---|---|
| 684557 | 4/1964 | Canada | 2/24 |
| 1123157 | 5/1982 | Canada | 2/24 |
| 672513 | 5/1952 | United Kingdom | 2/24 |

Primary Examiner—Edgar S. Burr
Assistant Examiner—Huong Q. Pham
Attorney, Agent, or Firm—Thomas Hooker

[57] ABSTRACT

A knee brace provides support elements and impact protection in pockets fastened to the outside of the tubular sleeve of the brace. The pockets hold at least two pads, namely an annular pad which bears through the sleeve to engage around the patella, and a protective covering pad over the annular pad. A pocket panel holds one or more support pads on the sides of the brace, preferably both sides. The pads are hollow tubes with sealed ends, joined to one another long coextensive webs.

11 Claims, 1 Drawing Sheet

KNEE BRACE

BACKGROUND OF THE INVENTION

1. Field of the Invention

This invention relates to a protective and/or therapeutic support for encircling the knee joint to give support and protection to the skeletal, muscular and surface structures of the knee, and more particularly to an elastic knee brace which includes side pockets with insertable stiffeners or supports and an annular pad to engage the kneecap.

2. Description of the Prior Art

Individuals who has sustained knee injuries, or who have had operations on their knees, or who have weak knee joints, commonly are required to wear knee braces, either continuously or when indulging in strenuous activities. Knee pads are also commonly used by athletes and by persons with minor leg and knee injuries. Typically, a circumferentially stretchable elastic sleeve can be pulled on over the foot or wrapped around the leg and attached at its ends, to encircle a person's knee. The sleeve provides inward compressive force tending to support the knee joint (i.e., the junction of the femur, tibia and fibula and patella) against hyper-displacement that could stretch and injure the ligaments and tendons of the leg. The front central portion of the sleeve can be provided with an opening through which the user's patella or kneecap projects, particularly when the knee is bent. U.S. Pat. No. 4,201,203 to Applegate discloses a sleeve-type knee brace with an opening in the front. A drawstring in an elastic casing facilitates adjustment of the circumference of the opening. Lateral pads located on opposite sides of the fixed opening and other pads provide additional protection for the user's knee.

Barlow, in U.S. Pat. No. 4,250,578 discloses a knee brace with pocket-like members at the patella and areas adjacent the patella. It includes extra pads for impact/abrasion protection of the patella and side areas, but no structure ensures that the any pad in the pockets remains centered over or engaged with the patella.

In U.S. Pat. No. 4,115,902 to Taylor, another sleeve-type knee brace includes side hinge braces which are carried in pocket-like members and are secured by means of belts at the top and bottom of the knee brace. Plastic stiffeners also may be added.

Most sleeve-type knee braces concentrate on support of the knee ligaments and muscles involved in hinging motion of the knee. The typical cut-away patella section in these braces makes the knee easier to bend by allowing the patella to protrude but deprives the patella itself of protection from impact or abrasion. Most kneebraces concentrate on plastic or rigid stiffeners to act as knee-hinge-stiffening braces disposed at the sides of the joint. Known braces do not include at the same time substantial provision for impact absorption, abrasion protection and structural support of all the structures associated with the knee.

SUMMARY OF THE DISCLOSURE

The device of this invention combines support for all the knee bones and connective tissues with impact protection thereof in a knee brace comprising a resilient tube enclosing a user's knee and leg adjacent the knee. The tube has a three compartment pocket with a central compartment positioned over the kneecap and two side compartments. All three compartments are preferably sewn shut to hold in place supports and protective elements. The side compartments carry resistant stiffeners that support the knee yet allow supported flexing of the knee. The central compartment carries a patella centering brace which engages the user's kneecap through the tube material, and a second pad over the annular pad for general impact and abrasion protection.

It is, therefore, an object of this invention to provide both support and impact absorption of the knee.

It is another object of this invention to provide a knee brace which includes an annular patella-engaging cushion.

It is still another object of this invention to provide a knee brace which includes a three compartment pocket with knee supports in the compartments.

It is yet another object of this invention to provide a knee brace in which the support elements are resilient to absorb impact forces.

These and other objects will be more readily ascertainable to one skilled in the art from a consideration of the following figures, description and exemplary embodiments, with the understanding that the drawings are illustrative only and that changes may be made in the specific construction illustrated and described within the scope of the appended claims.

BRIEF DESCRIPTION OF THE DRAWING(S)

DETAILED DESCRIPTION OF THE PREFERRED EMBODIMENT(S)

Figure 1:
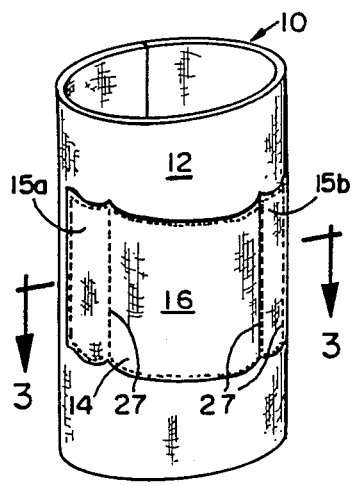
FIG. 1 is an isometric view of the assembled knee pad of this invention.

Referring now to the drawings, and more particularly to FIG. 1, the assembled knee brace 10 is shown in isometric view. Sleeve 12 is generally a flexible tube, preferably constructed of a foamed-resin elastomer such as neoprene, with a fabric surface layer. An external partitioned pocket 14 is formed by attaching a divided panel to the front of the sleeve 12. The panel 14 is preferably also fabric-covered neoprene. The neoprene for each of these layers can be, for example, about $\frac{3}{8}$ inch thick. Sectional pocket panel 14 is divided by stitching 27 which attaches panel 14 to the sleeve and creates three discrete sections: central section 16, which is dimensioned to completely cover the kneecap and define a wide central compartment; and two side sections 15, which define narrow vertically oriented side compartments located on the sides of the central compartment when the brace is being worn. Sleeve 12 is lightweight, flexible enough to be pulled over the knee into position and yet, by inclusion of pads and supports, strong enough to support an injured knee against hyper-extension of the joint or hyper-displacement of the patella, and protect the knee from impact and/or abrasion injuries.

The preferred neoprene/fabric structure of the brace is a closed tube. It will be appreciated, however, that the basic structure could also be an open linear band with buttons, hooks, hook-and-pile (Velcro) or other fasteners for attaching together free ends of the band after encircling the knee. In either case the result is a tube that encircles the knee and bears resiliently inwardly.

Figure 2:
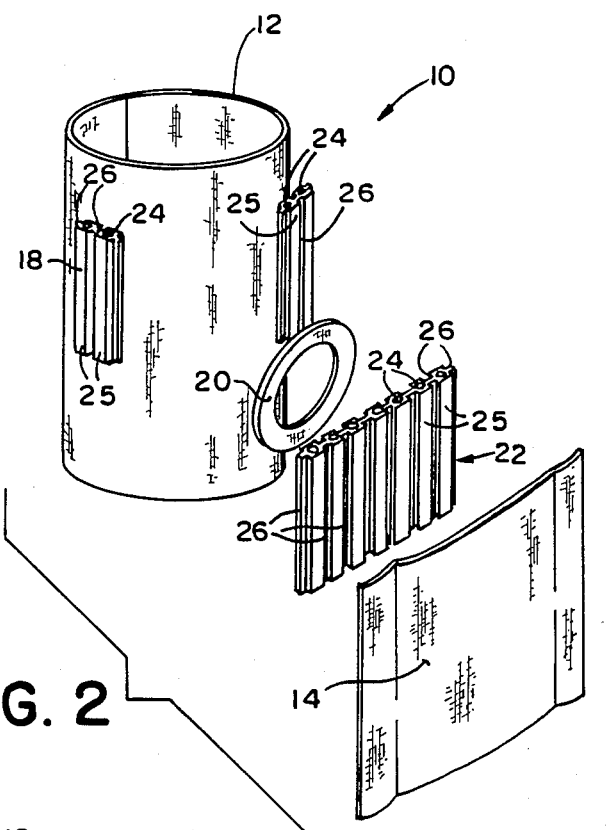
FIG. 2 is an exploded isometric view showing the sleeve, annular pad, pneumatic pads and pocket panel of the knee pad.
Figure 3:
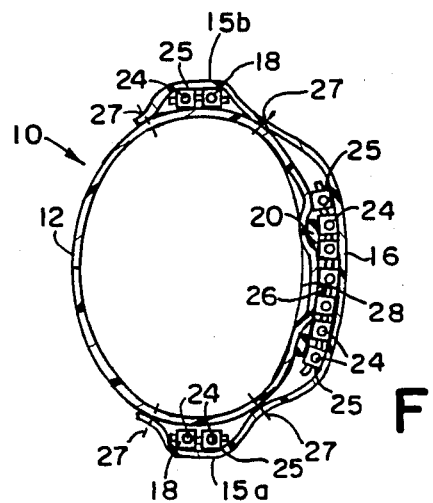
FIG. 3 is a section view taken along lines 3—3 in FIG. 1.

Now referring to FIGS. 2 and 3, an exploded view of knee brace 10 show the side supports 18, impact absorbing central pad 22, and annular kneecap pad 20, all enclosed in the central compartment between pocket-defining panel 14 and sleeve 12. Sleeve 12 has a diameter of approximately 4 to 6 inches and is capable of expanding to approximately 10 inches when stretched over the leg for positioning. Being neoprene (or like resilient material), sleeve 12 readily contracts at any point to its lesser diameter to give firm support to the knee notwithstanding variations in circumference of the leg at the knee, and to stay in position without slipping. This fixes the brace to the knee, unlike the smooth fabric of the traditional multi-layer wrapped bandage. Sleeve 12 is non-abrasive and moisture absorbent for comfortable long-term wear, being neoprene with absorbent fabric outer layers, a material commonly used for skindivers' wet suits.

Pocket panel 14 is preferably a unitary piece of fabric covered neoprene which is stitched directly onto sleeve 12, the stitching 27 (as seen in FIGS. 1 and 3) passing through panel 14 and sleeve 12, forming three completely closed pocket compartments 15a, 15b and 16. It is also possible to make one or more of the compartments openable, permitting replacement of the pads as necessary, for example, to reduce the stiffness of the support over time as an injury heals. The compartments can have closure flaps (not shown) for this purpose, the flaps being fixable to close the pockets by means of buttons, snaps, Velcro, etc. As required, and at least before panel 14 is stitched completely closed, supports 18a and 18b are inserted into side pocket compartments 15a and 15b respectively, when are then closed. The supports permit flexing of the knee, especially the hinging motion of the knee, and can be of a stiffness as appropriate in view of the particular injury or like to be treated. Supports 18a and 18b may be composed of at least two elongated, parallel, hollow pneumatic tubes 25. Each tube 25 is preferably generally rectangular in cross section and joined to the adjacent tube(s) 25 along one or both of its lateral exterior walls by a web 26 coextensive with the tube wall. The tubes are straight when at rest and resiliently resist bending. Each tube 25 is sealed at least at both tube ends, trapping air inside the tube to provide a pad which is stiffer than an openended hollow tube and also better resists compression. Thus although pads 18a and 18b are flexible, they resist impact compression and in combination with sleeve 12 resist bending of the knee.

It is possible to embody the invention with only one side support compartment, or to place a support in only one of two defined compartments. At least one side support is needed, but two are preferred, in compartments disposed diametrically opposite one another on the lateral sides of the knee. More than two supports are also possible, preferably all placed along the lateral sides of the knee.

Patella-covering pad 22 is composed of a plurality of identical sealed pneumatic tubes 25 joined by webs 26. Patella pad 22 is dimensioned to completely cover the kneecap and front of the knee and extends around approximately half of the circumference of sleeve 12. Pad 22 protects the patella from impact.

Annular pad 20 is placed between patella pad 22 and sleeve 12 to engage the circumference of the patella or the kneecap itself. The patella moves around somewhat on the knee in normal movements, although attached to the leg bones by ligaments. The annular pad 20 acts as a centering brace and restricts movement somewhat, urging the patella to remain substantially centered and thus reducing stress on the ligaments by which the patella is attached to the femur, tibia and fibula. Annular pad 20 is preferably cut from a layer of neoprene, which may be the same fabric covered neoprene as the sleeve and pocket, about ⅜ inch thick. When pressed inwardly by pad 22, patella-engaging pad 20 forms a toroidal bump 28 bearing through sleeve 12 around the patella. The annular pad 20 is pushed inwardly onto the knee by pressure from sleeve 12 and pad 22, and tends to surround and engage the patella of the user's knee, without adding a great deal of thickness to the knee brace. The central opening in pad 20 is the same size as the patella, thereby engaging it circumferentially all the way around. Accordingly, the patella becomes fixed in place and tends not to move out of correct position.

There are several variations which can be practiced in the scope of this invention. Although fabric covered neoprene has been preferred for each of the sleeve, pocket and annular pad 20, other soft yet stretch resistant materials are within the scope of this invention. The sealed pneumatic tube construction for the stiffeners and the patella pad are preferred because the tubes provide both impact protection and bend resistance, but other padding may be suitable.

The knee brace of this invention is lightweight yet resistant to both impact and bending forces. It is comfortable and simple for the wearer to place and remove. Protective and supportive structures are included for all the bones and connective tissues at the knee.

The invention as disclosed is a knee brace comprising a resilient sleeve 12 sized to enclose a user's knee and adjacent leg portions. The sleeve 12 is either a closed tube or a band attachable at its ends to form a tube, and includes a pocket panel 14 which forms a closed pocket. Preferably the pocket is sectional and includes side compartment 15a and 15b and central compartment 16. At least one resilient support member is inserted into one or both of side compartments 15a and 15b. A resilient impact-resistant pad 22 is located in central compartment 16 and covers and extends beyond the user's patella. An annular pad 20, sized to engage the patella, is located between sleeve 12 and pad 22. The sleeve 12 and pad 20 are fabric covered neoprene. The supports 18a and 18b are pads comprising a plurality of elongated, sealed pneumatic tubes 28 joined to each other along lateral exterior walls by coextensive webs 26.

Having now illustrated and described the invention, it is not intended that such description limit this invention, but rather that this invention be limited only by reasonable interpretation of the appended claims.

What is claimed is:

1. A knee brace comprising:
  a resilient sleeve sized to enclose the knee and adjacent leg portions of a person wearing the brace, said sleeve including an overlying pocket panel secured to the sleeve, the sleeve and panel defining a wide compartment overlying the knee and at least one adjacent narrow compartment extending along one side of the wide compartment and along the knee;
  at least one narrow resilient support member fitted in the narrow compartment;
  a wide resilient, absorbing pad fitted in the wide compartment to overlie the knee; and, an annular pad, said annular pad being smaller than the wide pad and sized to closely surround the patella of the knee to locate, support and protect the patella, the annular pad being located in the center of the wide compartment between said sleeve and said wide pad.

2. The knee brace according to claim 1, including a second narrow compartment on the other side of the wide compartment and a second narrow resilient support member located in the second narrow compartment and extending along the knee.

3. The knee brace according to claim 1 wherein said sleeve and said pocket are made of material including neoprene.

4. The knee brace according to claim 3, wherein the neoprene is fabric covered.

5. The knee brace according to claim 1, wherein said impact absorbing pad comprises a plurality of identical, elongated, parallel, hollow pneumatic tubes, each said tube being generally rectangular in cross section and joined to an adjacent tube along one of its lengthwise exterior walls by a web coextensive with said tube ends, each said tube being sealed at both tube ends, trapping air inside each said tube to provide a pad which resists compression.

6. The knee brace according to claim 1, wherein each said support member comprises a pad composed of at least two identical elongated, parallel, hollow pneumatic tubes, each said tube being generally rectangular in cross section and joined to an adjacent tube along one of its lengthwise exterior walls by a web coextensive with said tube wall, each said tube being sealed at both tube ends, trapping air inside each said tube to provide a pad which resists compression.

7. A knee brace comprising:
a resilient band attachable over a user's knee to define a resilient tube;
a panel attached to the tube at spaced points to thereby define with the tube at least one pocket;
a patella-engaging annular pad in the at least one pocket, sized to closely surround and support a patella by forming an annular protrusion through the tube; and,
an impact absorbing pad in said pocket, the impact absorbing pad being disposed over the annular pad and protecting the knee from impact.

8. The knee brace according to claim 7, wherein the panel and band define three pockets, a central pocket holding the annular pad and the impact absorbing pad, and two lateral pockets disposed opposite one another on lateral sides of the knee.

9. The knee brace according to claim 8, further comprising a support member in at least one of the lateral pockets.

10. The knee brace according to claim 8, comprising support members in both said lateral pockets, at least one of the impact absorbing pad and the support members having a resilient hollow tube, sealed at opposite ends to trap air therein.

11. The knee brace according to claim 10, wherein the impact absorbing pad and each of the support members have a plurality of hollow tubes wherein each hollow tube is joined to an adjacent tube by a web.

* * * * *